United States Patent [19]

Suld et al.

[11] 4,207,080

[45] Jun. 10, 1980

[54] DIMERIZATION OF NORBORNADIENE TO EXO-EXO HEXACYCLIC DIMER

[75] Inventors: George Suld, Springfield; Abraham Schneider, Overbrook Hills; Harry K. Myers, Jr., Aston, all of Pa.

[73] Assignee: Suntech, Inc., St. Davids, Pa.

[21] Appl. No.: 640,107

[22] Filed: Dec. 11, 1975

[51] Int. Cl.$^2$ ............................ C10L 1/04; C07C 3/21
[52] U.S. Cl. ......................................... 585/22; 60/211; 60/215; 149/109.4; 585/1; 585/362
[58] Field of Search ................... 44/80; 60/211, 215; 260/666 PY; 149/109.4

[56] References Cited

U.S. PATENT DOCUMENTS

| | | | |
|---|---|---|---|
| 3,113,421 | 12/1963 | Koch | 60/211 X |
| 3,113,426 | 12/1963 | Smith et al. | 60/211 X |
| 3,165,887 | 1/1965 | Koch | 60/211 X |
| 3,242,667 | 3/1966 | Kidwell | 60/215 |
| 3,703,361 | 11/1972 | Konecky | 60/215 X |

Primary Examiner—Leland A. Sebastian
Attorney, Agent, or Firm—J. Edward Hess; Donald R. Johnson; Anthony Potts, Jr.

[57] ABSTRACT

Norbornadiene [bicyclo(2.2.1)heptadiene-2,5] is dimerized to the exo-exo stereoisomer of the hexacyclic dimer of norbornadiene at both an excellent selectivity and conversion using an effective amount of a three component catalytic system of diethylaluminum chloride, ferric or ferrous or cobaltic or cobaltous acetylacetonate and bis(1,2-diphenylphosphino)ethane. The reaction rate is rapid. After hydrogenation the exo-exo hexacyclic dimer can be used as a component of high energy fuel for either jet or rocket propulsion.

12 Claims, 1 Drawing Figure

THEORETICALLY POSSIBLE DIMERS OF NORBORNADIENE

PENTA-CYCLICS exo-t-exo    endo-t-endo    exo-t-endo    exo-c-exo    endo-c-endo    exo-c-endo

HEXA-CYCLICS endo-endo    exo-exo    exo-endo    endo-exo

HEPTA-CYCLICS

Binor-S

U.S. Patent
Jun. 10, 1980
4,207,080
THEORETICALLY POSSIBLE DIMERS OF NORBORNADIENE
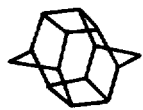
PENTA-CYCLICS: exo-t-exo, endo-t-endo, exo-t-endo, exo-c-exo, endo-c-endo, exo-c-endo
HEXA-CYCLICS: endo-endo, exo-exo, exo-endo, endo-exo
HEPTA-CYCLICS: Binor-S

DIMERIZATION OF NORBORNADIENE TO EXO-EXO HEXACYCLIC DIMER

The invention herein described was made in the course of or under a contract thereunder with the United States Air Force Systems Command.

CROSS REFERENCES TO RELATED APPLICATIONS

This application is related to applicants' U.S. patent application Ser. No. 640,102 and 639,742, both filed same date. The subject matter of the former is directed to the endo-endo stereoisomer of the hexacyclic dimer of norbornadiene and the latter is directed to a mixture of exo-endo and endo-endo stereoisomer of said dimer.

BACKGROUND OF THE INVENTION

This invention generally relates to mixtures resulting from the dimerization of norbornadiene. In particular, the invention relates to a mixture having a high concentration of a monoolefinic hexacyclic hydrocarbon known by the systematic chemical name of exo-exo stereoisomer of hexacyclo($7.2.1.0^{2,8}-.1^{3,7}.1^{5,13}.0^{4,6}$)tetradec-10-ene, (also designated as hexacyclo[$9.2.1.0^{2,10}.0^{3,8}.0^{4,6}.0^{5,9}$]tetradec-12-ene). The stereoisomer results from the catalytic dimerization of norbornadiene which is a $C_7H_8$ bicyclic, diolefinic hydrocarbon. More particularly, the invention relates to a mixture of high concentrations of the exo-exo form of the hexacyclic dimer. The latter is a $C_{14}H_{16}$, six-ring monoolefinic hydrocarbon. Also, the invention relates to a mixture of the foregoing which have been hydrogenated to convert the monoolefinic hexacyclics into completely saturated hexacyclics. Hydrogenation of monoolefinic hexacyclic dimer to the saturated dimer improves stability of the product towards oxidation thereby enhancing its utility as a high energy fuel. Completely saturated exo-exo hexacyclic dimer has utility as a component of high energy fuel.

An object of present invention is to provide a composition which has a maximum concentration of hexacyclic norbornadiene dimers and minimal concentration of pentacyclic norbornadiene dimers and other compounds. Also, the composition can be used as a component of a high energy fuel for use in either jet or rocket propulsion. Jet propulsion includes a jet engine which can be used for missile, plane and others and includes the three basic types, i.e., ramjet, turbo-jet and pulse jet. The term jet generally refers to a device requiring air whereas rocket generally refers to a device containing its own oxygen or oxidizing agent.

Another object of present invention is to provide a novel method for preparing the foregoing composition. Still another object is the dimerization of norbornadiene at both an excellent selectivity and conversion to the exo-exo form of the four possible stereoismeric hexacyclic dimers.

Norbornadiene is also known as bicyclo(2.2.1)-heptadiene-2,5. A method of preparation is disclosed in U.S. Pat. No. 2,875,256 issued Feb. 24, 1959. Norbornadiene is referred to as NBD hereinafter. NBD can be represented by either one of the following structural formulas:

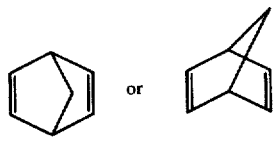

Dimerization of NBD is disclosed in U.S. Pat. No. 3,377,398, issued Apr. 9, 1968. The disclosed process results in the production of various dimer mixtures. The process therein involves the use of an iron catalyst system, e.g., ferric acetylacetonate and triethylaluminum, and a temperature above 140° C. The product of said method is a mixture which includes both the monoolefinic hexacyclic and diolefinic pentacyclic dimers. Said patent also disclosed that no dimerization occurs if the iron acetylacetonate of the catalyst system is replaced by cobalt acetylacetonate.

U.S. Pat. No. 3,282,663, issued Nov. 1, 1966, discloses the dimerization of NBD to both pentacyclic and hexacyclic dimers. In one example, tetrakis(triphenylphosphine)nickel is the catalyst, in another, iron acetylacetonate and triethylaluminum is the catalyst system. Use of cobalt acetylacetonte is suggested.

U.S. Pat. No. 3,326,992, issued June 20, 1967, discloses the partial hydrogenation of NBD dimer mixtures U.S. Pat. No. 3,326,993, issued June 20, 1967, discloses the dimerization of NBD, in the presence of a certain cobalt-containing carbonyl catalyst, to heptacyclic dimers. The resulting dimer mixture contains major proportions of the completely saturated dimer.

U.S. Pat. No. 3,329,732, issued July 4, 1967, discloses an improved method for the dimerization of NBD. The catalyst comprises certain metal salts of the tetracarbonylcobaltate anion wherein the metal is zinc, cadmium, mercury or indium. Resulting dimer mixture contains predominantly hexacyclic dimers.

Catalytic reaction of NBD and butadiene is disclosed in an article in The Journal of Organic Chemistry, January, 1970, Vol. 35, title, "Catalytic Norbornadiene-Butadiene and Norbornadiene-1,1-Dimethylallene Codimerization", by A. Greco, et al., pages 271–274. One of the disclosed catalysts is a three component system of tris(acetylacetonate)iron-AlEt$_2$Cl-bis(diphenylphosphino)ethane. AlEt$_2$Cl refers to diethylaluminum chloride. One of the dimers reported therein, i.e., Fig. 1e, has been identified as the exo-exo stereoisomer of the hexacyclic dimer of norbornadiene.

Also, a catalytic reaction of NBD is disclosed in an article in The Journal of the American Chemical Society, Vol. 94, July 26, 1972, starting page 5446, titled, "Dimerization and Trimerization of Norbornadiene by Soluble Rhodium Catalyst", by Nancy Acton et al.. This article discloses the exo-exo form of the hexacyclic dimer of NBD.

As the previous discussion indicates, many NBD dimers are possible. G. N. Schrauzer, in his review "On Transition Metal-Catalyzed Reactions of Norbornadiene and the Concept of a Complex Multicenter Processes" in Advances on Catalysis 18, 373 (1968) Acad. Press, describes the fourteen theoretically possible dimers of NBD. The possible dimers, grouped according to the number of their carbocyclic rings, are as shown in the accompanying drawing. Any and each of the dimers shown in the drawing have different physical and chemical properties.

The synthesis problem in the dimerization of NBD can be visualized from the number of possible isomers and that is to obtain both an excellent selectivity and conversion to a desired isomer.

The advantages of present invention are many. The production of the exo-exo hexacyclic form of the dimer is highly favored while the production of pentacyclics is strongly minimized. The latter are not desirable as high energy fuels because of their high melting points. Separation of pentacyclics from the hexacyclics is commercially not feasible. On the other hand, the exo-exo hexacyclic dimer can be easily separated from small amounts of unreacted feed and other products, particularly higher boiling polymers. Thus, a separated product can be obtained consisting essentially of the exo-exo material. The latter, after hydrogenation, provides a material which can be used as a component for high energy, high density fuel.

SUMMARY OF THE INVENTION

NBD is rapidly dimerzied to the exo-exo form of the $C_{14}H_{16}$ hexacyclic dimer at both an excellent selectivity and conversion. The dimerization requires an effective amount of a three component catalytic system of diethylaluminum chloride, ferric ferrous or cobaltic or cobaltous acetylacetonate and bis(1,2-diphenylphosphine)ethane. The three components are referred to hereinafter as DEAC, $FeA_3$, $FeA_2$, $CoA_3$, $CoA_2$ and Diphos respectively. Range of favorable temperatures is specified.

A mixture containing the foregoing $C_{14}H_{16}$ dimer and having a purity of 88 weight % as to the exo-exo form and after hydrogenation has a specific gravity @ 20/4° C. of 1.0675; net heat of combustion of 158,883 BTU/gallon; viscosity at 100° F. of 9.98 cs; and the melting point of its last crystal is +37° F. Net heat of combustion means the state of the water made is as a gas.

Surprisingly, a blend of hydrogenated exo-exo hexacyclic dimer concentrate and hydrogenated endo-endo hexacyclic dimer concentrate, obtainable by a different process described in our copending application Ser. No. 640,102, has a melting point of the last crystal which is substantially lower than said melting point for either dimer.

DESCRIPTION OF THE DRAWING

The accompanying drawing discloses the structures for the theoretically possible dimers of NBD. The dimers are grouped according to the number of their rings. Also shown, when applicable, are the isomeric prefixes.

DESCRIPTION

The catalytic dimerization of NBD via present invention can be represented by the following formula reaction:

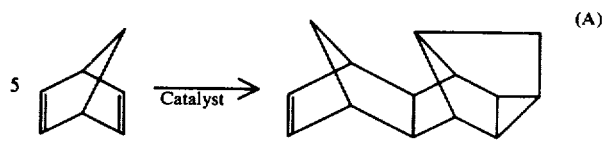

$C_7H_8$      $C_{14}H_{16}$
(I)         (II)
            exo-exo

Compund I is NBD while compound II is the $C_{14}C_{16}$ hexacyclic exo-exo dimer of NBD. The endo-endo stereoisomer of compound II has the following structure:

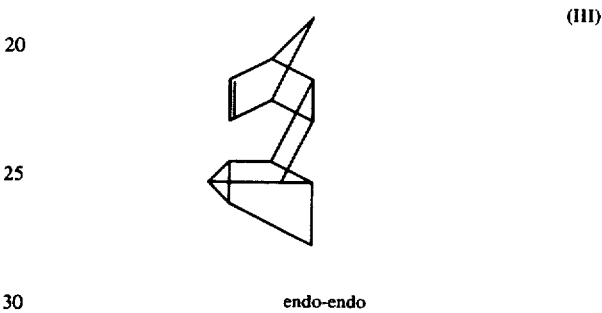

(III)

endo-endo

The product resulting from the foregoing reaction A, due to the specific catalyst and operating conditions, contains a major amount of compound II. The word product herein refers to only compounds formed as a result of the foregoing dimerization reaction A; it does not include unreacted feed. Thus, the product can contain minor amounts of other compounds such as pentacyclic dimers of NBD. Separation of compound II from the unreacted NBD catalyst and small amounts of heavier products is obtained by distillation. As one alternative the catalyst can be deactivated by the addition of a hydroxylic material, e.g., methanol. The various components form layers which can be separated and then compound II can be distilled from other hydrocarbons.

Generally, the product contains typically no more than about 10 mole % of pentacyclic dimers of NBD, more typically no more than about 5 mole %. Generally, the product contains a major amount of the exo-exo stereoisomeric form of the hexacyclic dimer of NBD. Under more favorable conditions the product contains typically at least about 60 mole % and more typically at least about 70% and even more typically at least about 80% of the dimer.

The catalytic system favoring reaction A contains three components. The three are DEAC, $FeA_3$ or $FeA_2$ or $CoA_2$ or $CoA_3$ and Diphos. The amount of the catalytic system present is an effective amount so that a suitable conversion to dimer occurs and the selectivity as to compound II is sufficient. Any material which during the dimerization reaction could adversely effect the catalyst system should not be present. For example the presence of hydroxylic compounds such as water, alcohol or oxygen from air could deactivate the catalyst system.

Selectivity refers to the amount of the particular copound formed divided by the amount of all compounds formed. Conversion to the dimer is the amount of total dimer formed divided by the sum of the total dimer plus reacted feed. From a commercial standpoint economics determines whether a particular conversion and/or selectivity is attractive.

The reaction time required for an economically satisfactory selectivity and/or conversion depends on many factors such as catalyst to NBD ratio as well as operating conditions. These factors are discussed hereinafter while typical conditions are provided by the Examples. However, surprisingly the reaction is rather rapid, for example, as reported hereinafter, in one run a 62% conversion was obtained in five minutes.

Within the catalytic system the mole amount of NBD relative to the mole amount of $FeA_3$ or $FeA_2$ or $CoA_2$ or $CoA_3$ can influence both the selectivity and conversion to compound II. This is shown by the results of certain runs discussed in the Examples. The data indicates that to obtain both excellent selectivity and conversion to compound II the mole ratio of NBD to $FeA_3$ or $FeA_2$ or $CoA_2$ or $CoA_3$ can be less than about 800. A preferred range of ratio of $NBD/FeA_3$ or $FeA_2$ or $CoA_2$ or $CoA_3$ is between from about 700 to about 50 and a more preferred range is from about 600 to about 100.

Another consideration of the catalytic system is the mole ratio of Diphos to $FeA_3$ or $FeA_2$ or $CoA_2$ or $CoA_3$. This ratio also influences both the selectivity and conversion to compound II. Results of various runs reported in the Examples demonstrate this. Generally, ratios as high as 4 and as low as 0.25 are effective, but for the lower value the reaction rate may be slow. Thus, a preferred range is between from about 3.9 to about 0.51 and a more preferred range is between from about 3 to about 0.75. Note that with only Diphos relatively no dimerization of NBD will occur.

DEAC is another component of the catalytic system. As the comparative data in the Examples indicate a similar reducing agent, triethylaluminum, is not satisfactory for the manufacture of predominantly the exo-exo form of the hexacyclic dimer. While the amount of DEAC in the system can vary substantially it generally varies relative to the amount of $FeA_3$ or $FeA_2$ or $CoA_2$ or $CoA_3$ used. An effective mole ratio range of DEAC to $FeA_3$ or $FeA_2$ or $CoA_2$ or $CoA_3$ is between about from 3 to about 25 with about 5 to 20 preferred and about 7 to 15 more preferred. Excess DEAC also serves as a scavenger for any water and/or oxygen in the feed. Generally, however, whenever DEAC is used, it is advantageous to conduct the reaction under substantially anhydrous conditions.

A suitable solvent can be used in the dimerization reaction. Since the dimerization reaction A is exothermic the solvent can serve as a heat sink. It can also solubilize the reaction components, that is, it can dissolve the feed and catalyst and thereby obtain good mixing. The solvent should not adversely react with the feed, products or catalyst. Also, a solvent facilitates the handling of the reaction mixture. Classes of suitable solvents include aromatic hydrocarbons, cycloparaffins, halogenated aromatics, halogenated paraffins and halogenated cycloparaffins. Specific examples include benzene, toluene, xylenes, cyclohexane, chlorobenzene, bromobenzene, and the like. As to the amount of solvent used, excessive amounts decrease the reaction rate. Such a dilution can adversely affect the economics for a commercial operation.

Selective dimerization of NBD occurs in a liquid phase therefore it is not desirable to have the reaction temperature largely exceed the boiling points of the NBD, products or solvent. Conversely, if the temperature is much below the optimal temperatures the dimerization rate would be too low to be economically feasible. An operable temperature range is between from about 40° C. to about 100° C. with 50°–100° C. a preferred range. The operating pressure can vary substantially, generally however, it can range from atmospheric to up to about 2000 psi, with 1000 psi a preferred upper value. Process economics favor operating at lower pressures, however, moderately elevated reaction pressure may be desirable to keep gaseous reaction components in solution.

The selective NBD dimerization of the present invention can be carried out in either a batch or continuous process.

The product resulting from the aforementioned dimerization reaction A can be hydrogenated using a hydrogenation catalyst such as $PtO_2$ (Adams catalyst). The product generally would be hydrogenated after separation from the catalyst. After the separation the product can be fractionated and the concentrate containing the exo-exo hexacyclic dimer hydrogenated. However, the product can also be hydrogenated prior to fractionation. The purpose of the catalytic hydrogenation is to saturate the olefinic bond of the exo-exo hexacyclic stereoisomer of the NBD dimer and in particular any olefinic bonds contained in the product. In general compounds with olefinic bonds are not desirable in fuels, in part, because of their tendency to form gums and like materials, which can adversely effect the working of mechanical parts. Other problems also can be caused by compounds with olefinic bonds. Thus, the degree of hydrogenation should be sufficient to prevent the aforementioned problems. Furthermore, the length of time the product is stored influences the desired degree of necessary hydrogenation. In addition, certain additives, such as oxidation inhibitors, can be used to supplement the effect of hydrogenation. Generally, however, the degree of saturation is such that the monoolefinic hexacylic NBD dimers are converted essentially completely to saturated hexacyclic hydrocarbons. It is preferred that the extent of hydrogenation be such that the conversion is complete as determined by the infra-red technique.

To further illustrate the invention, the following examples are provided along with a comparative example.

EXAMPLES

Accompanying Table I and II summarize most of the dimerization runs which were carried out in 50 milliliter pyrex test tubes enclosed with wired serum caps fitted with an internal immersion thermometer. Additional runs, not included in the summary confirmed typical conclusions, for example, that conversions at a particular temperature increased with time.

A typical working procedure was as follows. First the tubes were flushed with argon. Then the materials were added to the tubes in the following order, $FeA_3$, solvent (either mixed xylenes and/or toluene), Diphos, NBD (99% pure), and DEAC (in n-octane) all at room temperature. This sequence was satisfactory and it is believed that other additional sequences should give substantially similar results. The amounts used are given in the Tables. In many of the runs the Diphos was in an 0.125 M solution in toluene and the DEAC was in a 1.1

M solution in tolune. Prior to use, the NBD (Aldrich, 99% pure) was percolated through alumina.

The test tubes were heated in an oil bath with the temperatures for the given runs indicated in the Tables. The conversions and selectivities reported in the Tables are based on analysis performed by vapor phase chromatography, on both packed and capillary columns.

Other NBD dimerization runs were conducted in larger reactors and in a somewhat different procedure. Thus, the data reported in Table IV was obtained in 250 milliliter Fischer Porter glass pressure reactors. Also the temperatures of the reactions were varied throughout the runs and the autogenous reaction pressures were measured. Table V is a summary of the temperatures and pressures throughout Run 19. This table also reports the changes noted in the color of the reaction mixture. The information reported in Table V is indicative of similar data obtained for the other runs, i.e., 20 and 21.

In Table I comparisons of Runs 1 and 2 indicate a slight decrease in conversion at given conditions if the ratio of NBD/FeA$_3$ increases. Comparison of Runs 1 and 3 indicates that changing the ratio of Diphos/FeA$_3$ from 4 to 1 substantially increases the conversion. Comparison of Runs 3 and 4 indicates again that decreasing the ratio of NBD/FeA$_3$ causes an increase in conversion. Runs 5, 6 and 7, compared to the previous runs, indicate that increasing the temperature from 70° C. to 85° C. increases conversions while still maintaining good selectivity. Comparison of runs 7 and 8 shows the advantage of having present a relatively low ratio of NBD/FeA$_3$. Runs 9 and 10 indicate the adverse effect of lowering the ratio of Diphos/FeA$_3$ on conversion. Runs 11 and 12 indicate that reduction of temperature from 70°-85° C. to 50° C. decreases conversion.

The data in Table I also indicates that reaction rate is rather rapid. For example, in Run 3 the conversion was 62% after 5 minutes.

In Table II Runs 13–18 show the adverse effect on conversion of increasing the amount of solvent used or of lowering the ratio of Diphos/FeA$_3$. Influence of temperature on conversion is also shown. Also, Runs 16–18 demonstrate the decreased selectivity to the exo-exo dimer with a reaction temperature of 80° C. and low ratios of Diphos/FeA$_3$.

Accompanying Table III discloses additional runs made at Diphos/FeA$_3$ and NBD/FeA$_3$ ratios different than those previously reported.

Accompanying Table IV reports typical temperatures and pressures taken during Run 19 along with observations as to typical changes in the color of the reaction mixture. Similar changes were noted for runs 20 and 21. Also, this table shows the composition of the gas sample from the reaction mixture was taken. The sample analyzed about 93% ethylene. After the sample was taken the reaction vessel was vented and the pressure dropped to about 10 psig.

Compound II has a melting point of −1° C. and a latent heat of fusion of 6.52 calories per gram. Both values were determined by differential scanning calorimetry.

A liquid concentrate of Compound II, i.e., a mixture containing 88 wt.% of the exo-exo form of the hexacyclic dimer of NBD was hydrogenated in the following manner. A 500 cc Parr glass reactor was charged with 0.1 grams of Adams catalyst, i.e., PtO$_2$, 10.33 grams of the mixture and 25 milliliters of a solvent, i.e., methylcyclohexane. Hydrogen, at 50 psig, was fed to the reactor and the mixture was agitated by shaking. The temperature was ambient. After 10.5 minutes the hydrogen was stopped, the mixture removed from the reactor. The catalyst was then separated from the liquid concentrate. A sample of the hydrogenated dimer showed no residual double bonds by infra-red. In addition, vapor phase chromatography was used to follow the hydrogenation progress.

The melting point of the last crystal of the hydrogenation concentrate was +37° F. Other properties were as follows: specific gravity @20° C./4 of 1.0675; a net heat of combustion of 158,883 BTU/gal. and a viscosity @100° F. of 9.98 cs.

Samples of the foregoing exo-exo dimer concentrate were blended with samples of a concentrate of hydrogenated compound III which was prepared by a different process as disclosed in our copending application Ser. No. 640,102. The hydrogenated dimer concentrate contained, by weight, 93% of compound III before hydrogenation. The melting point of its last crystal was +37° F. and its other properties were as follows: specific gravity @20° C./4 of 1.0814; a net heat of combustion of 160,781 BTU/gal. and a viscosity @100° F. of 13.59 cs.

Surprisingly, as shown in Table V, the melting points of the last crystal of the blends of the two concentrates were lower than said melting point for either concentrate. Thus, for example, a blend of 35% exo-exo (II) concentrate and 65 endo-endo (III) concentrate has a melting point of last crystal of −52.6° F. Such a low value is advantageous when the blend is used as a high density, high energy fuel in a low temperature environment.

Additional runs were made in a similar fashion to those given in Table I, however, CoA$_3$ was used in lieu of FeA$_3$. Accompanying Table VI discloses the data obtained from these additional runs. Comparison of run 24 with runs 23 and 22 indicate that as the ratio of Diphos/CoA$_3$ increases the selectivity as to the exo-exo stereoisomer increases. Comparison of runs 22, 23 and 24 indicate that at some level the Diphos/CoA$_3$ ratio maximizes the conversion at the specified conditions.

Another run, i.e., 25, was made using 0.392 millimoles of CoA$_3$, 0.98 millimoles of Diphos, 294 millimoles of NBD, 12.25 millimoles of DEAC (10% in toluene), and sufficient toluene solvent to bring the solvent total to 33.18 milliliters. The temperature of this run was gradually raised from room temperature to about 73° C. at which temperature the reaction seemed to progress relatively fast. The lower temperature at which the reaction seemed to start was about 50° C. Run 25 was maintained at about 73° C. for 137 minutes at which time the heating was stopped. The following morning the catalyst was deactivated with a 10% sulfuric acid solution whereby two layers formed. The top organic layer was removed and analyzed. Conversion was 28.4%. The selectivities were as follows: 18.4% exo-endo, 75.1% exo-exo, 0.6% Binor-S, 0.9% endo-t-endo ( a pentacyclic) and two unknowns (1.5% and 3.5%) which were not pentacyclics. Run 25 shows the favorable selectivities as to the exo-exo stereoisomer of NBD.

Results, analogous to the foregoing, will be obtained if the aforementioned FeA$_3$ or CoA$_3$ is replaced by FeA$_2$ or CoA$_2$.

It should be noted that the feed to the foregoing reaction A consists essentially of NBD. Thus, for example, additional reactive monoolefinic and diolefinic hydrocarbons should be generally excluded.

COMPARATIVE RUNS

Accompanying Table VII contains data for additional runs (C3-C5) which were made in an analogous fashion to the aforementioned runs but with the exception that triethylaluminum (TEA) was used in the place of DEAC (Runs C1-C2). The conditions of the runs, amounts of catalyst and feed, conversions and selectivities were as shown in Table VII. Comparison of these runs C1 to C5 indicates that the use of DEAC in the catalyst system, as compared to TEA, favors the formation of the exo-exo hexacyclic dimer and suppresses the formation of pentacyclic dimers. In contrast, the use of TEA favors the formation of pentacyclic dimers and the endo-endo and exo-endo stereoisomers of hexacyclic dimers.

TABLE I

Conversion and Selectivities of Various Runs[3]

| Run | Temp. °C. | FeA$_3$[1] | Diphos[1] | Diphos/FeA$_3$ | NBD/FeA$_3$ | DEAC[1] | Time | % Conv. | % Selectivity exp[2] | endo[2] |
|---|---|---|---|---|---|---|---|---|---|---|
| 1 | 70 | 0.075 | 0.30 | 4 | 400 | 0.75 | 30 | 3.6 | — | — |
|   |    |       |      |   |     |      | 120 | 4.4 | 86 | — |
| 2 | 70 | 0.038 | 0.15 | 4 | 800 | 0.38 | 30 | 1.3 | — | — |
|   |    |       |      |   |     |      | 120 | 2.4 | 97 | — |
| 3 | 70 | 0.075 | 0.075 | 1 | 400 | 0.75 | 5 | 62 | — | — |
|   |    |       |      |   |     |      | 30 | 67 | 77 | — |
|   |    |       |      |   |     |      | 90 | 70 | — | — |
|   |    |       |      |   |     |      | 120 | 70 | 77 | — |
| 4 | 70 | 0.038 | 0.038 | 1 | 800 | 0.38 | 30 | 27 | — | — |
|   |    |       |      |   |     |      | 60 | 29 | — | — |
|   |    |       |      |   |     |      | 90 | 31 | 84 | — |
|   |    |       |      |   |     |      | 120 | 31 | 87 | — |
| 5 | 85 | 0.075 | 0.30 | 4 | 400 | 0.75 | 30 | 2.0 | — | — |
|   |    |       |      |   |     |      | 120 | 4.3 | 98 | — |
| 6 | 85 | 0.038 | 0.15 | 4 | 800 | 0.38 | 30 | 11 | — | — |
|   |    |       |      |   |     |      | 60 | 13 | — | — |
|   |    |       |      |   |     |      | 90 | 16 | — | — |
|   |    |       |      |   |     |      | 120 | 20 | 85 | — |
| 7 | 85 | 0.075 | 0.075 | 1 | 400 | 0.75 | 30 | 63 | — | — |
|   |    |       |      |   |     |      | 60 | 73 | — | — |
|   |    |       |      |   |     |      | 90 | 76 | 83 | — |
|   |    |       |      |   |     |      | 120 | 71 | 93 | — |
| 8 | 85 | 0.038 | 0.038 | 1 | 800 | 0.38 | 30 | 28 | — | — |
|   |    |       |      |   |     |      | 60 | 32 | — | — |
|   |    |       |      |   |     |      | 90 | 33 | 82 | — |
|   |    |       |      |   |     |      | 120 | 32 | 89 | — |
| 9 | 70 | 0.075 | 0.037 | 0.5 | 400 | 0.76 | 30 | 22 | 86 | — |
|   |    |       |      |   |     |      | 60 | 23 | — | — |
|   |    |       |      |   |     |      | 90 | 29 | — | — |
|   |    |       |      |   |     |      | 120 | 31 | 90 | 8.8 |
| 10 | 85 | 0.075 | 0.037 | 0.5 | 400 | 0.76 | 30 | 29 | 73 | 27 |
|    |    |       |      |     |     |      | 60 | 36 | — | — |
|    |    |       |      |     |     |      | 90 | 38 | — | — |
|    |    |       |      |     |     |      | 120 | 40 | 83 | 15 |
| 11 | 50 | 0.075 | 0.075 | 1 | 400 | 0.37 | 30 | 15 | — | — |
|    |    |       |      |   |     |      | 60 | 20 | — | — |
|    |    |       |      |   |     |      | 90 | 27 | — | — |
|    |    |       |      |   |     |      | 120 | 34 | 88 | 3.3 |
| 12 | 50 | 0.075 | 0.038 | 0.5 | 400 | 0.37 | 30 | 7 | — | — |
|    |    |       |      |     |     |      | 60 | 11 | — | — |
|    |    |       |      |     |     |      | 90 | 17 | — | — |
|    |    |       |      |     |     |      | 120 | 18 | — | — |

[1] Units are millimoles.
[2] exo = exo-exo; endo = endo-endo; both $C_{14}H_{16}$ hexacyclic dimers of NBD.
[3] Other conditions = 30 millimoles of NBD, 1 milliliter solvent (total).

TABLE II

Influence of Amount of Solvent and Diphos/FeA$_3$ Ratios on Conversions and Selectivities[1]

| Run | Diphos/FeA$_3$ | Solvent Milliliters | Conversion at °C. 60 | 70 | 80 | % Selectivity 60 Exo[2] | Endo[2] | 70 Exo[2] | Endo[2] | 80 Exo[2] | Endo[2] |
|---|---|---|---|---|---|---|---|---|---|---|---|
| 13 | 1 | 1.1 | 37 | 39 | — | — | — | 82 | 18 | — | — |
| 14 | 1 | 2.2 | 29 | 32 | — | 86 | 14 | 85 | 15 | — | — |
| 15 | 0.5 | 1.1 | 25 | 22 | 27 | 85 | 15 | 83 | 17 | 71 | 29 |
| 16 | 0.5 | 2.2 | 25 | 20 | 21 | 84 | 16 | — | — | 68 | 32 |
| 17 | 0.25 | 0.8 | — | — | 16 | — | — | — | — | 63 | 37 |
| 18 | 0.25 | 1.6 | — | — | 16 | — | — | — | — | 67 | 33 |

[1] Conditions, time = 120 minutes, = 30 millimoles of NBD, 0.06 millimoles FeA$_3$, 1 millimole DEAC.
[2] Exo = Exo Exo; Endo = Endo Endo; both $C_{14}H_{16}$ hexacyclic dimers of NBD.

TABLE III

Conversions and Selectivities of Runs in Large Batches

| Run | Diphos/FeA₃ | NBD/-FeA₃[1] | Temp. °C. | Time Min. | % Conversion to Dimer | % Selectivity Exo-Exo | Endo-Endo | Exo-Endo |
|---|---|---|---|---|---|---|---|---|
| 19 | 1.8 | 410 | 60–72 | 256[2] | 43 | 89 | — | — |
| 20 | 1.8 | 810 | 24–65 | 1171 | 23 | 87 | 0.9 | 6.1 |
| 21 | 1.3 | 550 | 21–58 | 900 | 26 | 96 | — | — |

[1] Amounts of feed used is as follows: (19) 493 millimoles; (20) 987 millimoles; (21) 715 millimoles.
[2] Difference between this value and that shown in Table V is that this time reflects just reaction time, whereas Table V includes times other than reaction time.

TABLE IV

Temperature and Pressure Profile of Run 19

| Time | Temperature of Reaction | Bath | Pressure psig | Steps and Observation* |
|---|---|---|---|---|
| — | 30 | 24 | 0 | Mix I, II & III (russet) |
| 1 | 20 | 11 | 0 | Add IV; (purple) upon heating to yellow |
| 5 | 12 | 12 | 0 | Amber clear |
| 16 | 21 | 24 | 5 | Bright, clear, russet |
| 31 | 44 | 48 | 20 | — |
| 49 | 65 | 59 | 34 | Bright red russet |
| 59 | 65 | 62 | 34 | Gas sampled and then vented |
| 64 | 63 | 64 | 10 | Cloudy russet |
| 194 | 63 | 65 | 9.5 | — |
| 300 | 63 | 64 | 9.5 | Bright clear russet, END |

*I = FeA₃, II = Diphos, III = NBD, IV = DEAC

TABLE V

Melting Behavior of Blends of Hydrogenated Concentrates of Exo-Exo and Endo-Endo Hexacyclic Dimers of NBD

| Weight % of Concentrates Exo-Exo- | Endo-Endo | Melting Point of Last Crystal °F. | Pour Point °F. |
|---|---|---|---|
| 100 | 0 | +37 | — |
| 65 | 35 | +7.7 | — |
| 50 | 50 | −29 | — |
| 35 | 65 | −52.6 | −63 |
| 25 | 75 | −45.4 | −85 |
| 0 | 100 | +37 | — |

TABLE VI

Conversions and Selectivities Using CoA₃[a]

| Run | Ratio of Diphos/CoA₃ | % Conversion | % Selectivity Exo-Exo | Binor-S[b] |
|---|---|---|---|---|
| 22 | 0.5 | 29.5 | 51 | 41 |
| 23 | 1.5 | 36.1 | 85.5 | 5 |
| 24 | 4 | 25.6 | 94.0 | 0 |

[a] Other catalyst components include 0.02 millimoles of CoA₃ and 0.29 millimoles of DEAC; the reaction was maintained at 60° C. for about 60 minutes, but samples for analysis were taken the following day. 9.8 millimoles of NBD were used.
[b] Binor-S is a heptacyclic dimer of NBD.

TABLE VII

Comparative Runs Using TEA and DEAC

| RUN NUMBER | C1 | C2 | C3 | C4 | C5 |
|---|---|---|---|---|---|
| Catalyst % Feed, millimoles | | | | | |
| FeA₃ | 0.5 | 1.2 | 1.0 | 2.0 | 2.0 |
| Diphos | 1.0 | 2.0 | 2.0 | 3.0 | 3.0 |
| Diphos/FeA₃ | 2/1 | 1.7/1 | 2/1 | 1.5/1 | 1.5/1 |
| NBD | 247 | 493 | 1184 | 789 | 789 |
| NBD/FeA₃ | 500/1 | 408/1 | 1184/1 | 395/1 | 395/1 |
| DEAC | 10 | 20 | — | — | — |
| TEA | — | — | 20 | 20 | 20 |
| Conditions | | | | | |
| Time, min. | 230 | 300 | 200 | 20 | 100 |
| Temp. °C. | — | 63 | 60 | 41 | 52 |
| % Conversion | 61 | 43 | 31 | 47 | 65 |
| % Selectivity | | | | | |
| 5 member rings | | | | | |
| Exo-t-exo | — | — | 26.4 | 28.8 | 39.7 |
| Endo-t-endo | 3.6 | 4.1 | 2.4 | — | 3.7 |
| 6 member rings | | | | | |
| Exo-endo | 8.3 | 5.9 | 14.2 | 28.3 | 23.9 |
| Exo-exo | 84.0 | 87.5 | 7.9 | 0.5 | 1.8 |
| Endo-endo | 0.1 | — | 44.1 | 36.4 | 26.0 |
| Unknown | 1.6 | 2.4 | — | — | — |
| Total | 97.6 | 95.8 | 95.0 | 94.0 | 95.1 |

The invention claimed is:

1. Process for dimerizing norbornadiene comprising:
    (a) contacting a feed consisting essentially of norbornadiene in the presence of an effective amount of a three component catalytic system of diethylaluminum chloride, ferric or ferrous or cobaltic or cobaltous acetylacetonate and bis(1,2-diphenylphosphino)ethane;
    (b) the contacting occurring within a temperature range between from about 40° C. to about 110° C; and
wherein an exo-exo form of a hexacyclic dimer of norbornadiene is the major product.

2. Process according to claim 1 wherein the mole ratio of norbornadiene to the acetylacetonate is less than about 800.

3. Process according to claim 2 wherein the mole ratio of bis(1,2-diphenylphosphino)ethane to the acetylacetonate is in the range between from about 3.9 to about 0.51.

4. Process according to claim 3 wherein the mole ratio of diethylaluminum chloride to the acetylacetonate is in the range between from about 3 to about 25.

5. Process according to claim 1 wherein the mole ratio of bis(1,2-diphenylphosphino)ethane to the acetylacetonate is in the range between from about 3 to about 0.75 and the mole ratio of norbornadiene to the acetylacetonate is between from about 700 to about 50 and the mole ratio of diethylaluminum chloride to the acetylacetonate is in the range of from about 5 to about 20.

6. Process according to claim 5 whereby the product contains no more than about 10 mole % of pentacyclics.

7. Process according to claim 6 wherein the product contains at least about 70 mole % of the exo-exo form of the hexacyclic dimer of norbornadiene.

8. Process according to claim 1 whereby the product contains no more than about 10 mole % of pentacyclics.

9. Process according to claim 8 whereby the product contains at least about 70 mole % of the exo-exo form of the hexacyclic dimer of norbornadiene.

10. A blend consisting essentially of saturated hexacyclic dimers of norbornadiene having a sufficient amount of both endo-endo and exo-exo forms of said dimers whereby said blend has a melting point of its last crystal low enough to permit use of the blend as a high energy fuel.

11. Blend according to claim 10 wherein the melting point of the last crystal is in the range between from about −10° F. and about −60° F.

12. Blend according to claim 11 wherein the blend contains the saturated exo-exo form of the hexacyclic dimer of norbornadiene in an amount ranging from about 25 to about 50 weight % and the saturated endo-endo form of the dimer in an amount ranging from about 75 to about 5 weight %.

* * * * *